United States Patent
Qian et al.

(10) Patent No.: US 9,580,420 B2
(45) Date of Patent: Feb. 28, 2017

(54) PROCESS FOR THE PREPARATION OF 4-(8-(2-CHLOROPHENOXY)-[1,2,4]TRIAZOLO[4,3-A]PYRIDIN-3-YL)BICYCLO[2.2.1]HEPTAN-1-OL AND NOVEL INTERMEDIATES THEREFOR

(71) Applicant: BRISTOL-MYERS SQUIBB COMPANY, Princeton, NJ (US)

(72) Inventors: Xinhua Qian, Flemington, NJ (US); Keming Zhu, Somerset, NJ (US); Joerg Deerberg, Columbus, NJ (US); Wendy Wangying Yang, Plainsboro, NJ (US); Kana Yamamoto, Toledo, OH (US); Matthew R. Hickey, Yardley, PA (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 0 days.

(21) Appl. No.: 14/817,352

(22) Filed: Aug. 4, 2015

(65) Prior Publication Data
US 2016/0039813 A1 Feb. 11, 2016

Related U.S. Application Data

(60) Provisional application No. 62/033,695, filed on Aug. 6, 2014.

(51) Int. Cl.
| | |
|---|---|
| *C07D 213/77* | (2006.01) |
| *C07C 35/29* | (2006.01) |
| *C07D 471/04* | (2006.01) |
| *C07C 29/00* | (2006.01) |
| *C07C 51/29* | (2006.01) |
| *C07C 61/13* | (2006.01) |

(52) U.S. Cl.
CPC ............ *C07D 471/04* (2013.01); *C07C 29/00* (2013.01); *C07C 35/29* (2013.01); *C07C 51/29* (2013.01); *C07C 61/13* (2013.01); *C07D 213/77* (2013.01); *C07C 2102/42* (2013.01)

(58) Field of Classification Search
CPC .... C07D 471/04; C07D 213/77; C07C 29/00; C07C 35/29; C07C 51/29; C07C 61/13
USPC .......................................................... 546/119
See application file for complete search history.

(56) References Cited

U.S. PATENT DOCUMENTS

| | | | | |
|---|---|---|---|---|
| 6,008,234 A | * | 12/1999 | Kochanny | C07D 401/12 514/328 |
| 7,579,360 B2 | | 8/2009 | Li et al. | |
| 2006/0281750 A1 | * | 12/2006 | Li | C07D 471/04 514/248 |
| 2010/0144744 A1 | * | 6/2010 | Li | C07D 513/14 514/249 |

FOREIGN PATENT DOCUMENTS

WO WO 2014159794 * 10/2014

OTHER PUBLICATIONS

Adcock; J. Org. Chem. 1984, 49, 1387-1397.*
Li; ACS Med. Chem. Lett. 2014, 5, 803-808.*
Webster; Expert Opin. Ther. Patents 2007, 17, 1407-1422.*
Grob; Helvetica Chimica Acta 1979, 62, 2802-2816.*
Chemical Abstracts STN Database Record for RN 1185307-52-1, database entry date Sep. 17, 2009.*
Gleiter; Helvetica Chimica Acta 1986, 69, 962-971.*
Lantos; Tetrahedron 1972, 28, 2507-2519.*
Wang; Bioorganic & Medicinal Chemistry Letters 2011, 21, 4146-4149.*

* cited by examiner

*Primary Examiner* — Noble Jarrell
*Assistant Examiner* — Daniel Carcanague
(74) *Attorney, Agent, or Firm* — Elliott Korsen

(57) ABSTRACT

A process is provided for preparing 4-(8-(2-chlorophenoxy)-[1,2,4]triazolo[4,3-a]pyridin-3-yl)bicyclo[2.2.1]heptan-1-ol and novel intermediates used in the process. The compound is a 11-beta hydroxysteroid dehydrogenase type I inhibitor which exhibits activity in the treatment of various metabolic diseases.

11 Claims, No Drawings

PROCESS FOR THE PREPARATION OF 4-(8-(2-CHLOROPHENOXY)-[1,2,4]TRIAZOLO [4,3-A]PYRIDIN-3-YL)BICYCLO[2.2.1]HEPTAN-1-OL AND NOVEL INTERMEDIATES THEREFOR

CROSS-REFERENCE TO RELATED APPLICATIONS

This application claims priority to U.S. Provisional Application Ser. No. 62/033,695, filed Aug. 6, 2014; the entire content of which is incorporated herein reference.

FIELD OF THE INVENTION

The invention generally relates to novel intermediates and an improved process for the preparation of 4-(8-(2-chlorophenoxy)-[1,2,4]triazolo[4,3-a]pyridin-3-yl)bicyclo[2.2.1] heptan-1-ol, a 11-beta hydroxysteroid dehydrogenase type I inhibitor which was recently in clinical trials for the treatment of type 2 diabetes, obesity, and the metabolic syndrome.

BACKGROUND OF THE INVENTION

The steroid hormone cortisol is a key regulator of many physiological processes. However, an excess of cortisol, as occurs in Cushing's Disease, provokes severe metabolic abnormalities including: type 2 diabetes, cardiovascular disease, obesity, and osteoporosis. Many patients with these diseases, however, do not show significant increases in plasma cortisol levels. In addition to plasma cortisol, individual tissues can regulate their glucocorticoid tone via the in situ conversion of inactive cortisone to the active hormone cortisol. Indeed, the normally high plasma concentration of cortisone provides a ready supply of precursor for conversion to cortisol via the intracellular enzyme 11-beta-hydroxysteroid dehydrogenase type I (11beta-HSD1).

11beta-HSD1 is a member of the short chain dehydrogenase superfamily of enzymes. By catalyzing the conversion of cortisone to cortisol, 11beta-HSD1 controls the intracellular glucocorticoid tone according to its expression and activity levels. In this manner, 11beta-HSD1 can determine the overall metabolic status of the organ. 11beta-HSD1 is expressed at high levels in the liver and at lower levels in many metabolically active tissues including the adipose, the CNS, the pancreas, and the pituitary. Taking the example of the liver, it is predicted that high levels of 11beta-HSD1 activity will stimulate gluconeogenesis and overall glucose output. Conversely, reduction of 11beta-HSD1 activity will downregulate gluconeogenesis resulting in lower plasma glucose levels.

Various studies have been conducted that support this hypothesis. For example, transgenic mice expressing 2× the normal level of 11beta-HSD1 in only the adipose tissue show abdominal obesity, hyperglycemia, and insulin resistance. (Masuzaki, H. et al., "A Transgenic Model of Visceral Obesity and the Metabolic Syndrome", *Science*, 294:2166-2170 (2001)). Conversely, when the 11beta-HSD1 gene is ablated by homologous recombination, the resulting mice are resistant to diet induced obesity and the accompanying dysregulation of glucose metabolism (Morton, N. M. et al., "Novel Adipose Tissue-Mediated Resistance to Diet-induced Visceral Obesity in 11β-Hydroxysteroid Dehydrogenase Type 1-Deficient Mice", *Diabetes*, 53:931-938 (2004). In addition, treatment of genetic mouse models of obesity and diabetes (ob/ob, db/db and KKAy mice) with a specific inhibitor of 11beta-HSD1 causes a decrease in glucose output from the liver and an overall increase in insulin sensitivity (Alberts, P. et al., "Selective Inhibition of 11β-Hydroxysteroid Dehydrogenase Type I Improves Hepatic Insuling Sensitivity in Hyperglycemic Mice Strains", *Endocrinology*, 144:4755-4762 (2003)). Furthermore, inhibitors of 11beta-HSD1 have been shown to be effective in treating metabolic syndrome and atherosclerosis in high fat fed mice (Hermanowski-Vosetka, A. et al., *J. Exp. Med.*, 202(4):517-527 (2005)). Based in part on these studies, it is believed that local control of cortisol levels is important in metabolic diseases in these model systems. In addition, the results of these studies also suggest that inhibition of 11beta-HSD1 will be a viable strategy for treating metabolic diseases such as type 2 diabetes, obesity, and the metabolic syndrome.

Lending further support to this idea are the results of a series of preliminary clinical studies. For example, several reports have shown that adipose tissue from obese individuals has elevated levels of 11beta-HSD1 activity. In addition, studies with carbenoxolone, a natural product derived from licorice that inhibits both 11beta-HSD1 and 11beta-HSD2 (converts cortisol to cortisone in kidney) have shown promising results. A seven day, double blind, placebo controlled, cross over study with carbenoxolone in mildly overweight individuals with type 2 diabetes showed that patients treated with the inhibitor, but not the placebo group, displayed a decrease in hepatic glucose production (Andrews, R. C. et al., *J. Clin. Endocrinol. Metab.*, 88:285-291 (2003)). This observation is consistent with the inhibition of 11beta-HSD1 in the liver. The results of these preclinical and early clinical studies strongly support the concept that treatment with a potent and selective inhibitor of 11beta-HSD1 will be an efficacious therapy in patients afflicted with type 2 diabetes, obesity, and the metabolic syndrome.

SUMMARY OF THE INVENTION

There are disclosed improved processes for the preparation of 4-(8-(2-chlorophenoxy)-[1,2,4]triazolo[4,3-a]pyridin-3-yl)bicyclo[2.2.1]heptan-1-ol, of formula I:

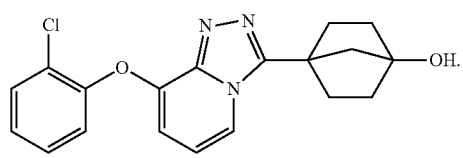

Compound I, compositions comprising Compound I, and methods of using Compound I are disclosed in U.S. Pat. No. 7,579,360 B2, which is assigned to the present assignee and is incorporated herein by reference in its entirety.

DETAILED DESCRIPTION OF THE INVENTION

In a first aspect, the invention provides a process for preparing Compound I of the formula:

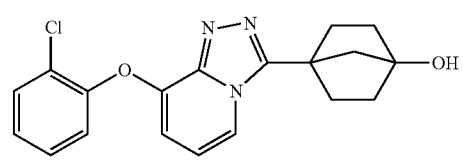

employing novel intermediates of the structures

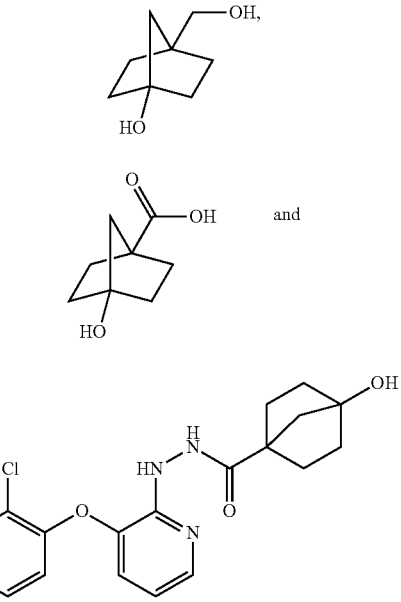

and to processes for preparing the novel intermediates.

Compound I is a 11-beta hydroxysteroid dehydrogenase type I inhibitor which has been in clinical trials and exhibits utility for the treatment of type 2 diabetes, obesity, inflammatory diseases, metabolic syndrome and cardiovascular related diseases.

In accordance with the present invention, a process is provided for preparing a triazolopyridine 11-beta hydroxysteroid dehydrogenase type I inhibitor having the structure I

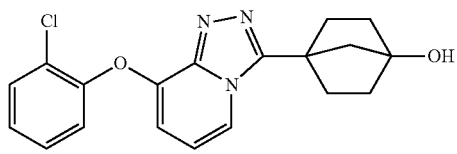

employing novel intermediates of the structures

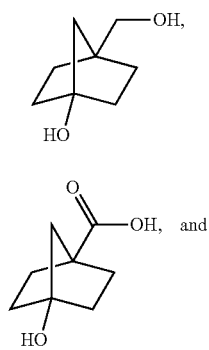

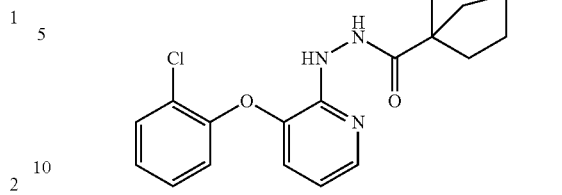

and to processes for preparing such novel intermediates.

The formula I compound inhibits activity of the enzyme 11-beta-hydroxysteroid dehydrogenase type I and thus is useful in treating disorders associated with such enzyme including diabetes, cardiovascular disease and inflammatory diseases as disclosed in U.S. Pat. No. 7,579,360, the disclosure of which is incorporated herein by reference.

In another aspect of the invention, a process is provided for preparing the primary alcohol intermediate of the structure

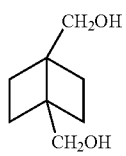

which includes the step of treating the dialcohol compound of the structure

with an aqueous mineral acid such as HCl or $H_2SO_4$.

In another aspect of the invention, a process is provided for preparing an acid intermediate of the structure

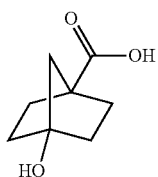

which includes the step of subjecting the primary alcohol of the structure

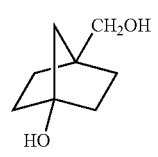

to oxidation to form the acid intermediate 2.

In still another aspect of the invention, a process is provided for preparing the pyridine hydrazide intermediate 3 of the structure

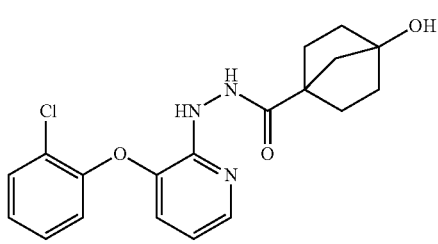

which includes the steps of reacting compound 2 with a hydrazide salt of the structure

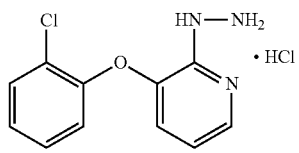

and 2-chloro-4,5-dihydro-1,3-dimethyl-1H-imidazoline chloride

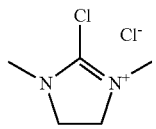

at a reduced temperature to form Compound 3.

In still another aspect of the invention, a process is provided for preparing compound I of the structure

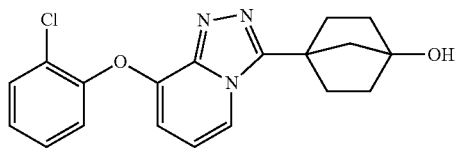

which includes the step of treating compound 3

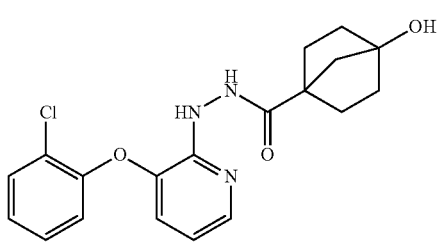

with a carboxylic acid to form compound I.

Novel compounds 1, 2 and 3 as well as the compound of formula I are prepared by the processes of the invention as outlined in the following reaction Schemes and description thereof. Exemplary reagents appear hereinafter and in the working Examples.

Scheme 1

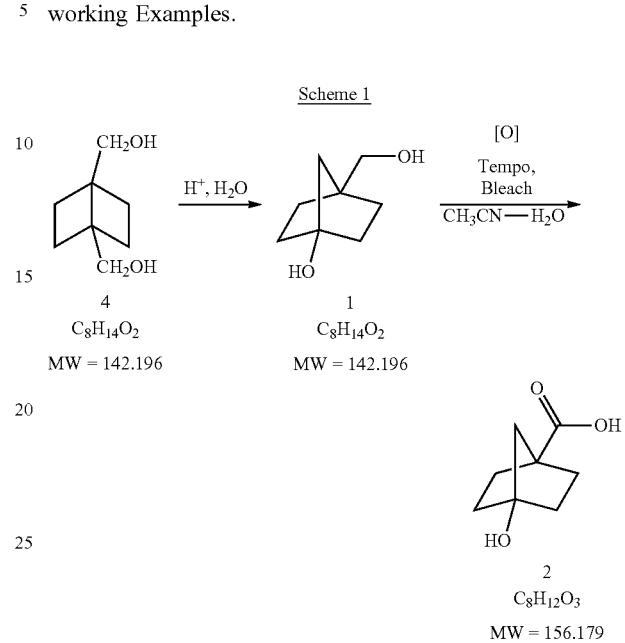

The dialcohol 4 is prepared as described in Lantos et al., "Propellanes-XV", *Tetrahedron,* 28:2507-2519 (1972).

The dialcohol 4 is treated with an aqueous mineral acid, such as HCl or $H_2SO_4$, and the reaction is heated to 75-85° C. with stirring until the reaction is complete. The reaction is cooled to 10-15° C. for neutralization and then adjusted to pH 11.0±0.2 with NaOH aqueous solution. IPA and NaCl are added and the mixture is stirred vigorously for >10 min. The phases are allowed to settle and are worked up to recover novel primary alcohol intermediate 1.

Compound 1 is then oxidized through the aldehyde 1a

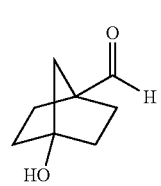

or to acid intermediate 2 utilizing sodium chlorite as an oxidant, a catalytic amount of 2,2,6,6-tetramethylpiperidine-N-oxide (TEMPO) and sodium hypochlorite. The reaction mixture is heated to 30-35° C. in $CH_3CN$ and sodium phosphate buffer (0.67 M, pH=6.7), followed by slow and simultaneous addition of a solution of sodium chlorite and a diluted bleach aqueous solution to prevent buildup of the oxidant.

After the reaction is completed, the mixture is cooled to 5-10° C., and the reaction pH is adjusted to 7.0-8.0 with NaOH. The reaction is quenched by either inverse addition to cold (0-5° C.) $Na_2SO_3$ solution or normal addition of $Na_2SO_3$ solution to reaction mixture while the batch temperature is maintained at <20° C. The pH of the aqueous layer increases to 8.5-10. After stirring for 2-3 hours at room temperature, the reaction mixture is extracted twice with MTBE to purge impurities. The organic layer is separated and discarded. The aqueous product rich layer is acidified with conc. HCl with stirring to pH 2.5-3.5. The product is extracted with MeTHF or ethyl acetate to give a solution of the crude carboxylic acid in 90-95% solution yield. Finally, compound 2 is crystallized from MeTHF or ethyl acetate (2-5 mL/g) and heptanes (7-10 mL/g) to produce a white crystalline product.

Besides sodium chlorite/TEMPO and sodium hypochlorite oxidation conditions, other oxidizing agents may be employed, such as trichloroisocyanuric acid (TCCA) with catalytic TEMPO/NaBr; TCCA with $RuCl_3$ as a catalyst; (Bis(acetoxy)-iodo)benzene (BAIB)/TEMPO in $CH_3CN$/water; BuOOH/CuCl in $CH_3CN$; 30% $H_2O_2$ in $CH_3CN$/water, and 30% $H_2O_2$/tungstate salts in water.

Referring to Scheme 2, novel intermediate 3 and the formula I compound are prepared as described below.

Scheme 2

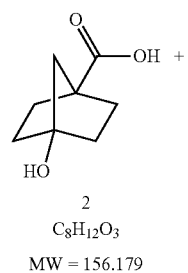

2
$C_8H_{12}O_3$
MW = 156.179

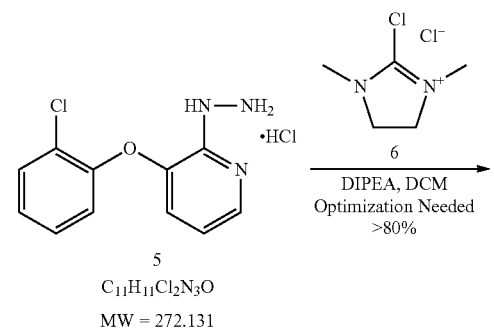

5
$C_{11}H_{11}Cl_2N_3O$
MW = 272.131

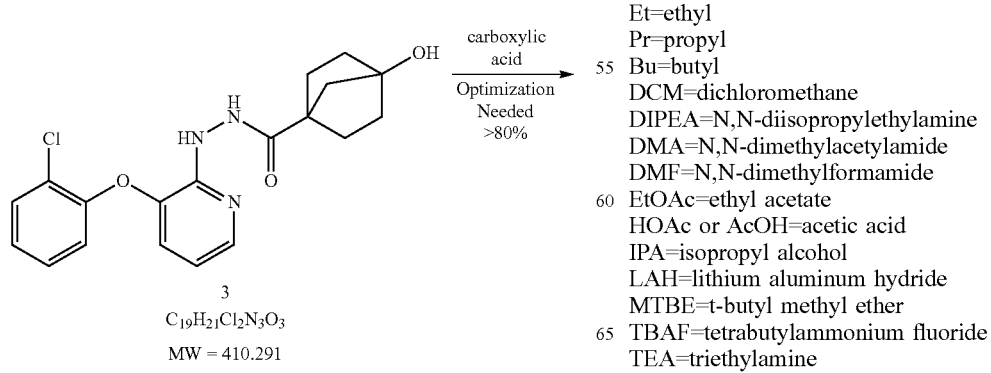

3
$C_{19}H_{21}Cl_2N_3O_3$
MW = 410.291

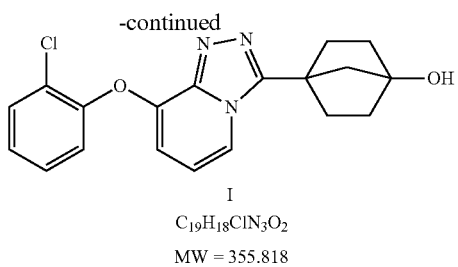

I
$C_{19}H_{18}ClN_3O_2$
MW = 355.818

Compound 2 is employed to prepare intermediate 3 as follows.

Compound 2 and dichloromethane are mixed together under an inert atmosphere and the resulting suspension is cooled to 0-5° C. with stirring. 2-Chloro-4,5-dihydro-1,3-dimethyl-1H-imidazolium chloride 6 is added and the resulting mixture is cooled to below 0° C. Diisopropylethylamine is added and then pyridine hydrazide HCl salt 5 (prepared as described in U.S. Pat. No. 7,579,360) is added and worked up to form intermediate 3.

Compound 3 may be used to form compound I (disclosed as Example 113 in U.S. Pat. No. 7,579,360) employing techniques disclosed in U.S. Pat. No. 7,579,360. Thus, compound 3 can be treated with a carboxylic acid such as benzoic acid in the presence of a suitable solvent such as 1-butanol and heated to 105-110° C. The reaction mixture is cooled and worked up to provide compound I.

EXAMPLES

The following Examples serve to further illustrate, but not limit, the present invention.

General

The term prep HPLC refers to an automated Shimadzu HPLC system using a mixture of Solvent A (10% MeOH/90% $H_2O$/0.2% TFA) and Solvent B (90% MeOH/10% $H_2O$/0.2% TFA). The preparative columns were packed with YMC or Phenomenex ODS C18 5 micron resin or equivalent.

Abbreviations

The following abbreviations are employed in the Examples and elsewhere herein:
Ph=phenyl
Bn=benzyl
i-Bu=iso-butyl
Me=methyl
Et=ethyl
Pr=propyl
Bu=butyl
DCM=dichloromethane
DIPEA=N,N-diisopropylethylamine
DMA=N,N-dimethylacetylamide
DMF=N,N-dimethylformamide
EtOAc=ethyl acetate
HOAc or AcOH=acetic acid
IPA=isopropyl alcohol
LAH=lithium aluminum hydride
MTBE=t-butyl methyl ether
TBAF=tetrabutylammonium fluoride
TEA=triethylamine
TFA=trifluoroacetic acid THF=tetrahydrofuran
equiv=equivalent(s)
min=minute(s)
h or hr=hour(s)
L=liter
mL=milliliter
μL=microliter
g=gram(s)
mg=milligram(s)
mol=mole(s)
mmol=millimole(s)
meq=milliequivalent
RT=room temperature
sat or sat'd=saturated
aq.=aqueous
TLC=thin layer chromatography
HPLC=high performance liquid chromatography
HPLC $R_t$=HPLC retention time
LC/MS=high performance liquid chromatography/mass spectrometry
MS or Mass Spec=mass spectrometry
NMR=nuclear magnetic resonance
mp=melting point Example 1

Preparation of Compound 1

A 3-necked 1-L reactor with an electric heating mantle, a mechanical (overhead) stirrer, a thermometer, a reflux condenser, and a distillation condenser were employed.

Procedure

Compound 4 (which can be prepared as described in Lantos et al., *Tetrahedron*, 28:2507-2519 (1972)) (40.0 g, GC potency ~98%, 276 mmol, 1.0 equiv.) was charged to the reactor. The reactor was charged with 1.0 N HCl (aq. 400 mL, 10.0 vol., ~1.5 equiv.) employing acid equivalent (1.0-2.0 equiv.) and an aqueous volume of about 5 to 40 vol. The mixture was heated to 80.0±5° C. with agitation until the reaction was completed. The reaction solution was cooled to 10-15° C. for neutralization and the solution pH adjusted to 11.0±0.2 (IPC-2) with 10.0 N NaOH aqueous solution (~40 mL). The reactor was charged with IPA (480.0 mL, 12 vol.) and NaCl salt (~50 g, made the aqueous solution half saturated) and the mixture was stirred vigorously for >10 min. The phases were allowed to settle and were worked-up to recover compound 1.

Example 2

Compound 1 was oxidized through the aldehyde 1a to acid intermediate 2 with sodium chlorite as an oxidant, a catalytic amount of 2,2,6,6-tetramethylpiperidine-N-oxide (TEMPO) and sodium hypochlorite. The reaction mixture was heated to 30-35° C. in $CH_3CN$ and sodium phosphate buffer (0.67 M, pH=6.7). This was followed by slow and simultaneous addition of a solution of sodium chlorite and a diluted bleach aqueous solution to prevent buildup of the oxidant and therefore reduce the risk of a runaway reaction. The addition was carried out as follows: add slowly and simultaneously 20% of the totally needed sodium chlorite solution and 20% of the totally needed dilute bleach and hold for at least 30 min. Then, the rest of the $NaClO_2$ solution and dilute bleach were added simultaneously over 2-3 hours. The reaction was slightly exothermic and completed in 7 to 16 hours at 30-35° C.

After the reaction was completed, the mixture was cooled to 5-10° C., and the reaction pH was adjusted to 7.0-8.0 with NaOH. The reaction was quenched by either inverse addition to cold (0-5° C.) $Na_2SO_3$ solution or normal addition of $Na_2SO_3$ solution to reaction mixture and batch temperature was maintained at <20° C. The pH of the aqueous layer increased to 8.5-10. After stirring for 2-3 hours at room temperature, the reaction mixture was extracted twice with MTBE to purge impurities. The organic layer was separated and discarded. The aqueous product rich layer was acidified with conc. HCl (~100 mL) with stirring to pH 2.5-3.5. The product was extracted with MeTHF or ethyl acetate to give a solution of the crude carboxylic acid in 90-95% solution yield. Finally, compound 2 was crystallized from MeTHF or ethyl acetate (2-5 mL/g) and heptanes (7-10 mL/g) to produce a white crystalline product with 80-85% isolated yields and >99.8% AP by GC.

Example 3

-continued

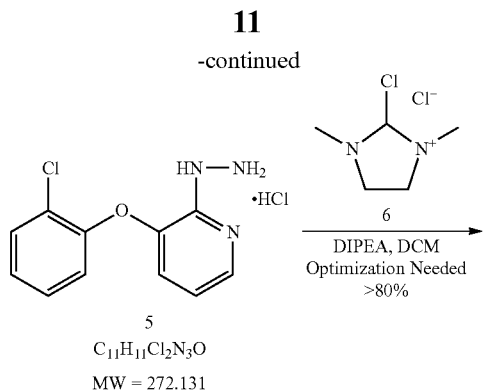

Compound 2 (1.00 equiv; 58.91 mmoles; 10.00 g) was charged into a 500 mL 3 neck flask with overhead stirring and N₂. Dichloromethane (92.69 equiv; 5.46 moles; 350.00 mL; 463.75 g) was added. The mixture was cooled to 0-5° C. while being stirred. 2-Chloro-4,5-dihydro-1,3-dimethyl-1H-imidazolium chloride 6 (DMC) (1.3 equiv (molar); 1.30 equiv; 76.58 mmoles; 12.95 g) was added. The mixture was held at −0.3° C. while being stirred for 1 h. Diisopropylethylamine (3 equiv (molar); 3.00 equiv; 176.72 mmoles; 30.82 mL; 22.84 g) was slowly charged. Compound 5 (0.9 equiv (molar); 0.90 equiv; 53.02 mmoles; 14.72 g) (prepared as described in U.S. Pat. No. 7,579,360) was added and the reaction mixture was held at 0-5° C. with stirring until reaction was completed (about 1 hour). 5 mL/g, 10 mL sat. NaHCO₃ solution (50 mL) was added and the mixture was warmed to 20-23° C. and held 10 min. The phases split and the solution was concentrated to dryness to obtain compound 3. 6 mL/g, 60 mL acetone was charged to dried compound 3 and the mixture was heated up to obtain a clear solution at ~46° C., and then cooled down slowly to 34-35° C. with stirring. The mixture was seeded with compound 3 and cooled to 20-23° C. and held for 2 h, and the cake filtered and washed with 10 mL of acetone and 20 mL of heptane. The reaction mixture was dried at 60° C. for 2 h to yield 14.5 g of compound 3 as a white solid, 65% yield with AP>99%.

Example 4

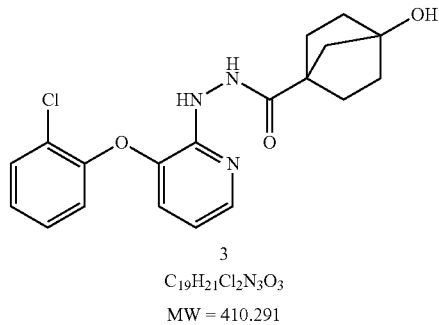

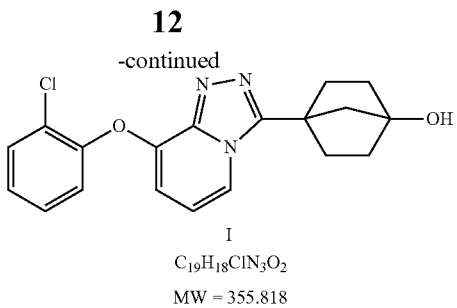

A 3-necked flask with overhead stirrer, oil bath, and N₂ purge line was charged with compound 3 (1.85 g; 1.00 equiv; 4.9 mmoles). 1-Butanol (101.0 mmoles; 9.3 mL; 7.5 g) was added to the reactor and then benzoic acid (6 equiv (molar); 29.7 mmoles; 3.6 g). The system was purged with N₂ and the pressure was kept on. The reaction was heated to 108° C. and monitored by HPLC: (273 nm, 15 µl to 10 ml, diluted with CH₃CN). The mixture was cooled to 20° C. The reaction was filtered to collect the product, washed with 5 ml of n-BuOH and 1.0 g of product cake collected, white color, HPLC AP 99.84. The ML and wash was continued to hold at 108° C. The mixture was cooled to 20° C. and 15 ml of n-heptane was charged. The clear solution was seeded with compound I and stirred for 30 min. Product I precipitated. The cake was washed with 5 ml of 3:1 heptane/EtOAc, dried under vacuum, and 0.315 of final product, Compound I, was obtained as a brown-colored cake (combined isolated yield 74.7%).

What is claimed is:
1. A compound of the structure

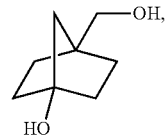

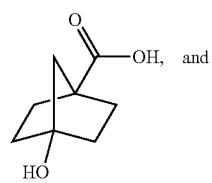

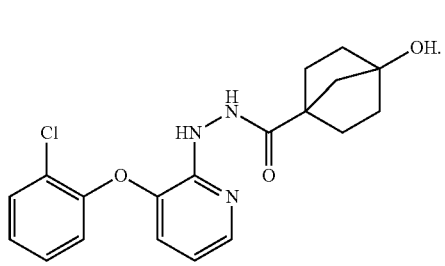

2. A compound according to claim 1 of the structure

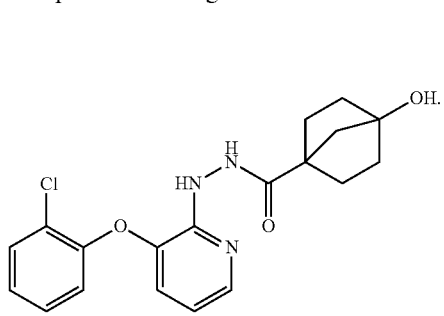

3. A process for preparing intermediate 1 of the structure

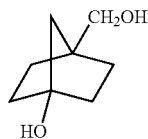

which comprises treating a dialcohol compound of the structure

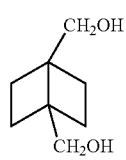

with an aqueous mineral acid selected from HCl and $H_2SO_4$.

4. A process for preparing Compound 2 of the structure

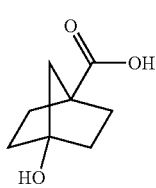

which comprises subjecting Compound 1 of the structure

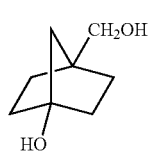

to oxidation to form the acid intermediate 2.

5. The process as defined in claim 4 wherein the aldehyde 1a

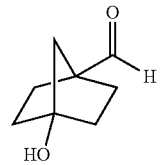

is formed as an intermediate.

6. The process as defined in claim 4 where the oxidation is carried out in the presence of sodium chlorite, 2,2,6,6-tetramethylpiperidine-N-oxide and sodium hypochlorite.

7. A process for preparing compound 3 of the structure

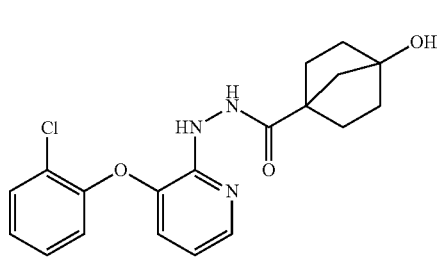

which comprises reacting the acid

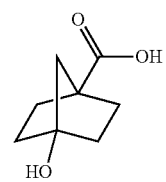

with a hydrazide salt of the structure

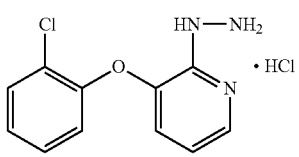

and 2-chloro-4,5-dihydro-1,3-dimethyl-1H-imidazoline chloride

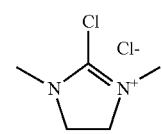

at a reduced temperature to form compound 3.

8. The process as defined in claim 7 wherein the reaction is carried out under an inert atmosphere at a temperature within the range from about 0 to about 5° C.

9. A process for preparing compound I of the structure

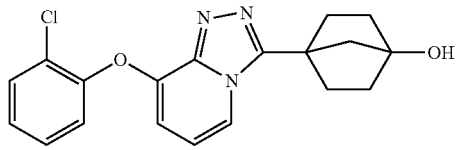

which comprises treating Compound 3 of the structure

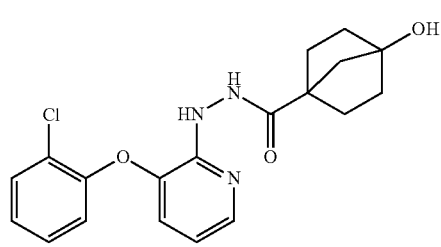

with a carboxylic acid to form compound I.

10. The process as defined in claim 9 wherein the carboxylic acid is benzoic acid and the reaction is carried out at a temperature within the range from about 105 to 110° C.

11. A process for preparing compound I of the structure

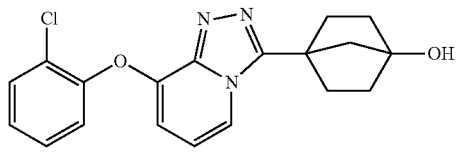

which comprises subjecting Compound 1 of the structure

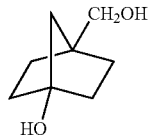

to oxidation to form compound 2

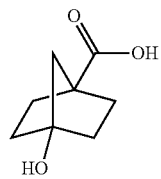

reacting compound 2 with a hydrazide salt of the structure

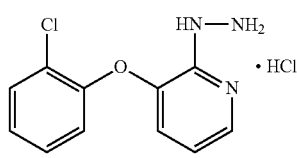

and 2-chloro-4,5-dihydro-1,3-dimethyl-1H-imidazoline chloride

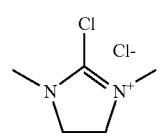

at a reduced temperature to form the pyridine hydrazide intermediate 3 of the structure

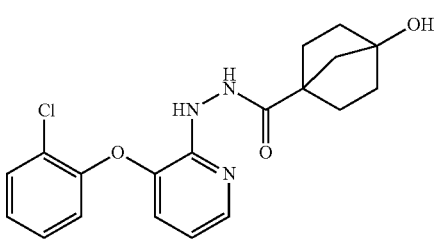

and treating compound 3 with a carboxylic acid to form Compound I.

* * * * *